(12) United States Patent
Choresh et al.

(10) Patent No.: US 8,114,631 B2
(45) Date of Patent: Feb. 14, 2012

(54) NUCLEIC ACIDS ENCODING SPIDER GLUE PROTEINS AND METHODS OF USE THEREOF

(75) Inventors: Omer Choresh, Tel Aviv (IL); Randolph V. Lewis, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 386 days.

(21) Appl. No.: 12/561,779

(22) Filed: Sep. 17, 2009

(65) Prior Publication Data
US 2010/0092538 A1   Apr. 15, 2010

Related U.S. Application Data

(60) Provisional application No. 61/097,839, filed on Sep. 17, 2008.

(51) Int. Cl.
*A61F 2/82* (2006.01)
*C07H 21/04* (2006.01)
*C07K 14/435* (2006.01)

(52) U.S. Cl. ...... 435/69.1; 424/423; 623/1.42; 536/23.5
(58) Field of Classification Search ............ None
See application file for complete search history.

(56) References Cited

U.S. PATENT DOCUMENTS
2007/0214520 A1   9/2007   Scheibel

FOREIGN PATENT DOCUMENTS
WO   2004/016651   2/2004

OTHER PUBLICATIONS
UniProt: A5WGU5_PSYWF, Jul. 10, 2007, http://genome.jp/dbget-bin/www_bget?uniprot:A5WGU5_PSYWF.

*Primary Examiner* — Kagnew H Gebreyesus
(74) *Attorney, Agent, or Firm* — Dann, Dorfman, Herrell & Skillman; Kathleen D. Rigaut

(57) ABSTRACT

Nucleic acids encoding spider glue proteins and methods of use thereof are disclosed.

16 Claims, 6 Drawing Sheets

```
ASG1
→
5'...gaacccgagtccagtccagtccagagaaacaccgagtccagaacaccgagaaacaccgag
3'...cttgggctcaggtcaggtcaggtctcttgtgctcttgtgctcttgtgctc
     G  S  V  G  L  G  S  V  S  S  G  S  V  G  L P  E  T  E  E  P  E  T  P  S  P  E  T  E  E  P  E  T  P  S
    tccagagaagaaccagaaacaccgagtccgagaagaaacaccgagtccgagaagaaacaccgagtc
    aggtctcttcttggtctttgtggctcaggctcttcttgtggctcttcttgtggctcag
     G  S  V  S  S  G  S  V  G  L  G  S  V  S  S  G  S  V  G  L  G P  E  T  E  E  P  E  T  P  S  P  E  T  E  E  P  E  T  P  S  P  E  T  E  E  P
    cagaagaaccagaaactgaaacaccgagccagaaacaccgagaaacagaagaaccc
    gtctcttgctcttgactttgtgctccggtctttgtgctccggtctttgtcttctttggg
     S  V  S  S  G  S  V  G  L  G  S  V  S  S  G  S  V  G  L  G  S  V  S  S  G E  T  P  S  P  E  T  E  E  P
    Gaaacaccgagtccagtccagaaacggaagaacca...3'
    ctttgtggctcaggtcgcctcttggt...5'
     S  V  G  L  G  S  V  S  S  G     ← ASG2
```

```
N. clavipes    EPETPSPETEEPETPSPETEEPETPSPETEEPETPSPETEEPETPSPETEEPETP
A. gemmoiedes  EPETLKPETKEPETLRPETEEPETPSPETEEPETP-----SPETEEPETPSPETEEPETP
               ****  ***  ****  ***************          ****************

N. clavipes    SPETEEPETPSPETEEPETPSPETEEPETPSPETEEPTTTPKPRVTAPETDCDENDVDCI
A. gemmoiedes  SPETEEPETPSPETEEPETPSPETEEPETPSPETEEPTTTPKPRVTAPETDCDENDVDCI
               ************************************************************

N. clavipes    IDDLGITPDWF
A. gemmoiedes  IDDLGITPDWF
               ***********
```

B

```
N. clavipes    GSSVSGLGVSGSSVSGLGVSGSSVSGLGVSGSSVSGLGVSGSSVSGLGVSGSSVSGLGVS
A. gemmoiedes  GSSVSGLGVSGSSVSGLGVSGSSVSGLGVSGSSVSGLGVSGSSVSGLGVSGSSVSGLGVS
               ************************************************************

N. clavipes    GLGVSGSSVSGLGVSGSSVSGLGVSGSSVSGLSVSGSSVSGFSVSGS
A. gemmoiedes  G-----SSVSGLGVSGSSVSGLGVSGSSVSGLSVSGSSVSGFSVSGS
               *     *****************************  *** ****
```

NUCLEIC ACIDS ENCODING SPIDER GLUE PROTEINS AND METHODS OF USE THEREOF

This application claims the benefit of priority under 35 U.S.C. §119(e) to U.S. Provisional Patent Application 61/097,839, filed on Sep. 17, 2008. The disclosure of the foregoing application is incorporated by reference in its entirety.

Pursuant to 35 U.S.C. §202(c), it is acknowledged that the U.S. Government has certain rights in the invention described, which was made in part with funds from the National Science Foundation, Grant Number CMS-0304494 and the National Institutes of Health, R01 grant EB000490.

FIELD OF THE INVENTION

This invention relates to the fields of molecular biology and biocompatible materials. More specifically, the invention provides isolated nucleic acids encoding spider glue glycoproteins having utility in biomedical and military applications.

BACKGROUND OF THE INVENTION

Several publications and patent documents are cited throughout the specification in order to describe the state of the art to which this invention pertains. Each of these citations is incorporated by reference herein as though set forth in full.

Spider silk has attracted scientists to study its unique mechanical properties and its potential to provide new bio-based materials for numerous applications ranging from protective clothing to medical products (1). However, one of the most intriguing spider biomaterials, yet one of the least explored, is the aqueous glue that coats the sticky-spiral threads of orb weaving spiders in order to retain prey in the web. It is considered one of the strongest and most effective biological glues (2-5). The aqueous coat is secreted from the orb weaving spider's aggregate glands and the gland's contents have been studied by several research groups (3-5). Chemical analysis of this complex aqueous solution shows relatively high concentrations of water-soluble organic compounds related to neurotransmitters, free amino acids, small peptides, low concentrations of various inorganic salts and glycoproteins. It has been suggested that the contents of this solution generates hygroscopic forces that may contribute to the thread stickiness, however studies identified the actual glue as microscopic nodules made of a glycoprotein (5). To date, almost nothing is known about the molecular structure and function of this glycoprotein.

SUMMARY OF THE INVENTION

In accordance with the present invention, novel nucleic acids are provided of SEQ ID NO: 1 and SEQ ID NO: 3 which encode the glycoprotein components of spider glue, e.g., SEQ ID NOS: 2 and 4. Methods of use spider glycoprotein glue are also disclosed.

It is an object of the present invention to provide a biological composition in which spider glycoprotein glue and a suitable carrier are combined together to form a distinctive and novel bioadhesive for administration to animals, including humans. The final spider glycoprotein glue and a biological carrier bioadhesive formulation may be achieved in a number of different ways, such as by premixing the spider glycoprotein glue and a biological carrier prior to application or administration, and then adding any remaining component(s) to form the spider glycoprotein glue in situ. In yet another embodiment, a chemically suitable carrier can be employed for nanotechnology applications.

It is a further object of the invention to provide a stable spider glycoprotein glue and a biological carrier sealing matrix which is inexpensive and safe and can be easily applied over a surgical or nonsurgical wound or opening, or injury site, or a graft site in a mammal, including humans, to promote, accelerate, and protect sealing and healing at and around the site. The spider glycoprotein glue and a biological carrier formulation remains at the site of application long enough to promote and protect the healing process. The spider glycoprotein glue and a biological carrier are generally metabolized during wound healing and do not trigger an adverse reaction, toxicity, or an immune response in the recipient animal.

It is another object of the invention to provide a spider glycoprotein glue-containing liposome composition in which medicaments or bioactive additives are encapsulated or entrapped in the liposomes. The liposomes serve as vehicles or carriers of the medicaments and additives at an injury site, surgical or nonsurgical opening, or wound. The contents of the liposomes are released at the site after application, either in a spontaneous or controlled fashion.

Another object of the invention is to provide a novel method for formulating spider glycoprotein glues to improve upon existing methods for better protection and treatment of surface wounds and surgical and nonsurgical openings.

A further object of the invention is to provide spider glycoprotein glue and a biological carrier as the basis for clot formation at the site of injury, surgery, or a wound while simultaneously providing the slow or rapid release of bioactive ingredients which are contained in the liposomes of the spider glue/liposome formulation. The formulation may comprise a number of different types of liposomes, each containing a different bioactive agent. Alternatively, the formulation may comprise a number of liposomes of a particular type, each containing different additives.

Another object of the invention is to provide a biologically compatible sealing agent comprising spider glycoprotein glue and a biological carrier optionally combined with liposomes to favor and maintain hemostasis following its use, even in heparinized individuals and in individuals suffering from coagulopathies. In addition, the spider glycoprotein glue and a biological carrier bioadhesive system of the invention should reduce the incidence of fistula formation and to decrease postoperative infections, tissue necrosis, and toxicity.

It is also an object of the invention to treat lumens in an individual with the glycoprotein glue and therapeutic agent formulations or stents coated with the same.

BRIEF DESCRIPTION OF THE DRAWINGS

FIG. 1 shows the nucleotide (SEQ ID NO: 1) and amino acid sequence (SEQ ID NO: 2) of the cloned spider glue glycoprotein ASG1. The 1221-bp clone contains an open reading frame encoding a 406 amino acid protein with a calculated molecular weight of 45221.7 daltons and isoelectric point of 4.22. The most likely potential O-glycosylation sites (Threonine or Serine) and an N-glycosylation site (Aspargine) are underlined. DNA and protein repeats are shaded. The gene sequence has been deposited to GenBank under accession number EU780014.

FIG. 2 shows the nucleotide (SEQ ID NO: 3) and amino acid sequence (SEQ ID NO: 4) of the cloned spider glue glycoprotein ASG2. The 2145-bp clone contains an open reading frame encoding a 714 amino acid protein with calculated size of 71548.3 dalton and isoelectric point of 4.10. The gene sequence has been deposited to GenBank under accession number EU780015.

FIG. 3 shows the DNA and protein sequences of both proteins. The repetitive domains of ASG1 (amino acids 208-324) and ASG2 (amino acids 545-660) are transcribed and translated on two different open reading frames from opposite strands of the same DNA sequence.

FIG. 4A: Hybridization with a probe complementary to asg1 detected an approximate 1200 bp transcript. FIG. 4B: Hybridization with a probe complementary to asg2 detected an approximate 2200 bp transcript.

FIG. 5A: Staining with highly specific glycoprotein stain (Pro-Q® Emerald 300 P21857, Molecular Probes) clearly shows that no glycoprotein band can be detected, which indicates that no glycoprotein has remained in the solution after the enzymatic treatment. FIG. 5B: Staining with total protein dye (SYPRO®Ruby S12001, Molecular Probes, OR, USA) shows two apparent deglycosylated glycoprotein bands (approximately 65 kDa upper band and 38 kDa lower, arrowed). The larger protein was cut out of the gel, purified and subjected to mass spectrometry analysis. Higher molecular size bands were shown to be remains of the deglycosylation enzymes in the solution that was loaded on the gel.

FIG. 6 shows an alignment comparison of the partial repetitive domains of ASG1 and ASG2 from two species of orb weaving spiders, *Nephila clavipes* and *Araneus gemmoides*. FIG. 6A: ASG1 shows 92% identity between species. FIG. 6B: ASG2 shows 91% identity between species.

DETAILED DESCRIPTION OF THE INVENTION

Figure 4:
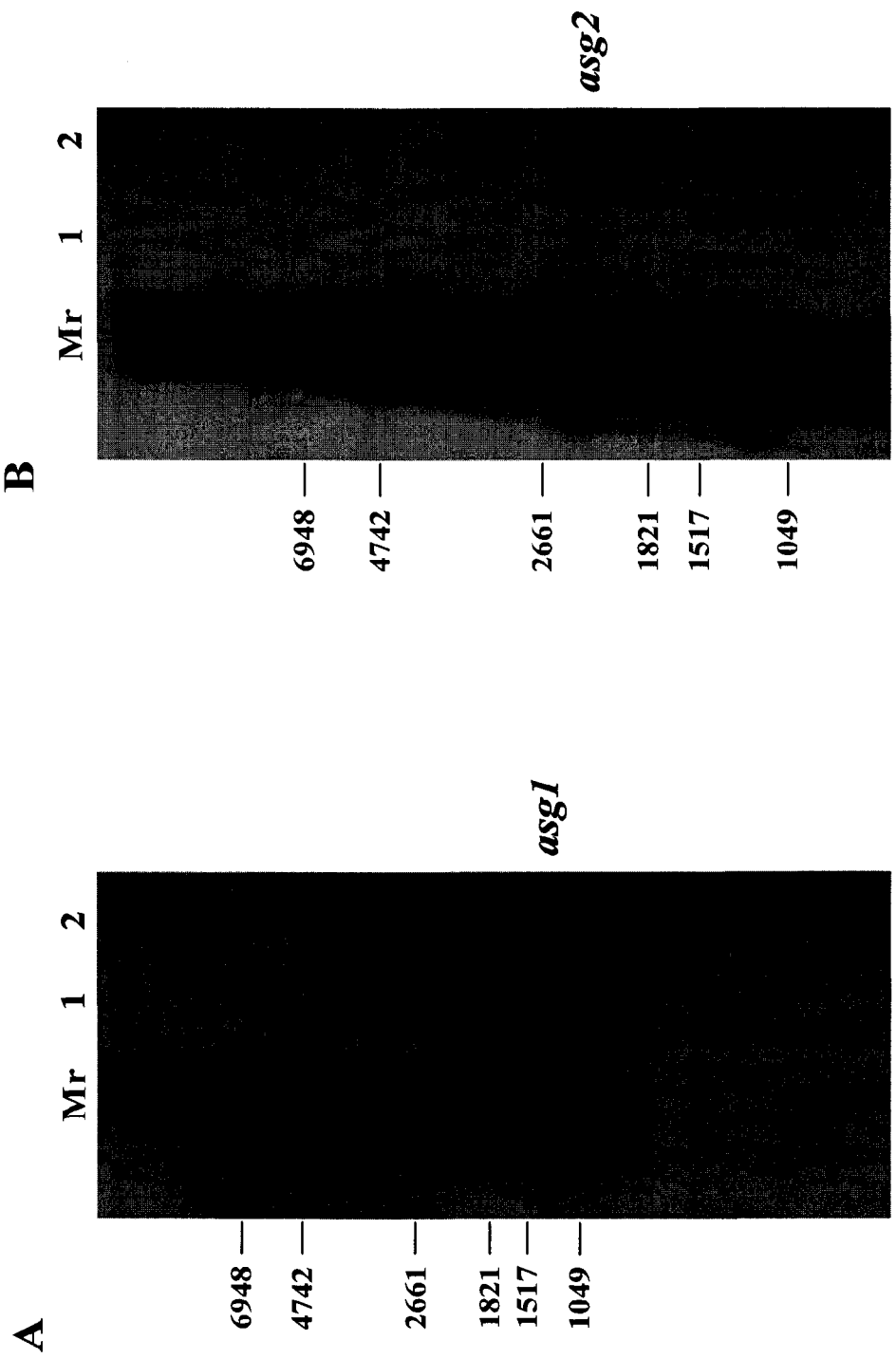
FIG. 4 depicts the results of northern blot analysis of the transcripts of asg1 and asg2 in the aggregate glands. Oligonucleotides were designed to be complementary to the repetitive DNA of each gene and were DIG-labeled. For each probe two samples of aggregate glands RNA were used: total RNA (lane 1) and messenger RNA (lane 2). Mr: DIG-labeled RNA marker indicating sizes in by (RNA1 11526529910, Roche Applied Science, IN, USA).

Substantial research has been done on the various silks that form the web of orb web spiders. However, success in prey capture depends as much on the web glue as on the silk fibers. Spider silk glue, which is considered one of the strongest and most effective biological glues, is an aqueous solution secreted from the orb weaving spider's aggregate glands and coats the spiral prey capturing threads of their webs. Studies identified the major component of the glue as microscopic nodules made of a glycoprotein. In accordance with the present invention, two newly discovered proteins that form the glue-glycoprotein of the golden orb weaving spider *Nephila clavipes* and the nucleic acids encoding them are provided. The results described herein demonstrate that both proteins contain unique 110 amino acid repetitive domains that are encoded on opposite strands of the same DNA sequence. Thus, the genome of the spider encodes two distinct yet functionally involved genes by using both strands of the same DNA sequence. Moreover, the closest match for the non-repetitive region of one of the proteins is chitin binding proteins. Thus, web glue appears to have evolved a substantial level of sophistication matching that of the spider silk fibers.

Accordingly, the present invention provides methods and compositions for the development of novel biologically-based biological glues for medical and commercial purposes.

Such purposes include, without limitation, utilizing the spider web glue of the invention in surgeries to replace sutures; applying the glue to biological traps for disinfestations; industrial application of the glue to micro- and nano-structures for adhering biological molecules such as DNA strands or protein threads to the surface thereof; fixing biological or tissue preparations (e.g., preparations made for different purposes such as in situ hybridization which cannot be covered with another glass), and adherence of spider silk products such as threads or films made of synthetic spider silk to other surfaces.

I. DEFINITIONS

For purposes of the present invention, "a" or "an" entity refers to one or more of that entity; for example, "a cDNA" refers to one or more cDNA or at least one cDNA. As such, the terms "a" or "an" "one or more" and "at least one" can be used interchangeably herein. It is also noted that the terms "comprising," "including," and "having" can be used interchangeably. Furthermore, a compound "selected from the group consisting of refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

As used herein, the phrases "spider glycoprotein glue," "spider web glue," and "biological glue" refer to the compositions comprising the novel nucleic acids encoding the asg1 and asg2 proteins described herein which can be used for a variety of purposes, for example, as sealants, delivery agents and adhesive compounds.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. This definition is synonymous and can be used interchangeable with "polynucleotide" when more than one nucleic acid is being referred to in the application. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

"Peptide" and "polypeptide" are used interchangeably herein and refer to a compound made up of a chain of amino acid residues linked by peptide bonds (also referred to as a "protein"). The sequence for peptides is given in the order from the amino terminus to the carboxyl terminus. A peptide or peptide fragment is "derived from" a parent peptide or polypeptide if it has the amino acid sequence that is identical or homologous to the amino acid sequence of the parent peptide or polypeptide. A "derivative" of a polypeptide or a fragment thereof means a polypeptide modified by varying the amino acid sequence of the protein, e.g. by manipulation of the nucleic acid encoding the protein or by altering the protein itself Such derivatives of the natural amino acid sequence may involve insertion, addition, deletion or substitution of one or more amino acids, and may or may not alter the essential activity of original the polypeptide. The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity and that may be present, for example, due to incomplete purification, addition of stabilizers, or compounding into, for example, immunogenic preparations or pharmaceutically acceptable preparations.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence is in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

"Bioadhesion" or "bioadhesive" as used herein refers to the ability of a material to adhere to a biological tissue for an extended period of time.

The term "functional" as used herein implies that the nucleic or amino acid sequence is functional for the recited assay or purpose.

The term "nanoparticle" refers to a particle having a size measured on the nanometer scale. As used herein, the "nanoparticle" refers to a particle having a matrix-type structure with a size of less than about 1,000 nanometers. When the nanoparticle includes a bioactive component, the bioactive component is entangled or embedded in the matrix-type structure of the nanoparticle. Nanoparticles include particles capable of containing a therapeutic agent that is to be released within a mammalian body, including specialized forms such as nanospheres, whether natural or artificial.

A "therapeutic agent" as used herein refers to an agent which can mitigate, cure, treat or prevent a disease or condition. It is synonymous with "medicament" and used interchangeably. It is particularly desirable that the therapeutic agent be capable of exerting it effect locally (i.e., at or near the site of the disease or condition). Exemplary therapeutic agents include, but are not limited to, antibiotics, anti-restenotics, anti-proliferative agents, anti-neoplastic agents, chemotherapeutic agents, cardiovascular agents, anti-inflammatory agents, immunosuppressive agents, anti-apoptotic and anti-tissue damage agents.

The term "treating" as used herein means the prevention, reduction, partial or complete alleviation or cure of a disease or condition.

The term "delivery" as used herein refers to the introduction of foreign molecule (i.e., protein containing nanoparticle) in cells. The term "administration" as used herein means the introduction of a foreign molecule (i.e., protein containing nanoparticle) into a cell. The term is intended to be synonymous with the term "delivery". Administration also refers to the methods of delivery of the compounds of the invention (e.g., routes of administration such as, without limitation, intravenous, intra-arterial, intramuscular, subcutaneous, intrasynovial, infusion, sublingual, transdermal, oral, or topical).

An "individual" as used herein refers to any vertebrate animal, preferably a mammal, and more preferably a human.

As used herein, "wound" includes surgical wounds, burns, ulcers, lacerations, and the like.

As used herein, "lumen" is defined as the space or cavity in the interior of a tubular structure or organ, such as an artery, vein, tube or duct, such as the bile duct.

A "therapeutic agent" as used herein refers to an agent that can mitigate, cure, treat or prevent a disease or condition. It is particularly desirable that the therapeutic agent be capable of exerting it effect locally (i.e., at or near the site of the disease or condition). Exemplary therapeutic agents include, but are not limited to, antibiotics, anti-restenotics, anti-proliferative agents, anti-neoplastic agents, chemotherapeutic agents, cardiovascular agents, anti-inflammatory agents, immunosuppressive agents, anti-apoptotic and anti-tissue damage agents.

As used herein, "pharmaceutical formulations" include formulations for human and veterinary use with no significant adverse effect. "Pharmaceutically acceptable carrier" as used herein refers to a composition or formulation that allows for the effective distribution of the agents of the instant invention in the physical location most suitable for their desired activity. The term "pharmaceutically acceptable carrier" means that the carrier can be taken into the subject with no significant adverse toxicological effects on the subject. The term "therapeutically effective amount" is the amount present that is delivered to a subject to provide the desired physiological response. Methods for preparing pharmaceutical compositions are within the skill in the art, for example as described in Remington's Pharmaceutical Science, 18th ed., Mack Publishing Company, Easton, Pa. (1990), and The Science and Practice of Pharmacy, 2003, Gennaro et al. A "pharmaceutically acceptable carrier" refers to a buffer, stabilizer or other material well known to those skilled in the art. Such materials should be non-toxic and should not interfere with the efficacy of the active ingredient. The precise nature of the carrier or other material may depend on the route of administration.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any spider glycoprotein encoding nucleic acid, but does not hybridize to other nucleotides. Also polynucleotide which "specifically hybridizes" may hybridize only to a spider glycoprotein glue encoding nucleic acid. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m=81.5° C.+16.6 \log [Na+]+0.41(\% G+C)-0.63(\% \text{formamide})-600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxy-ribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the spider glycoprotein glue encoding nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the spider glycoprotein encoding nucleic acid. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment which can be introduced into an individual or cell and may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "substantially pure" refers to a preparation comprising at least 50-60% by weight of a given material (e.g., peptide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

II. METHODS OF USING THE SPIDER GLYCOPROTEIN GLUE

The spider glue proteins of the invention may be expressed from their encoding nucleic acids, separately or together in single host organism. Once suitable quantities are produced, the glue components can be formulated in a suitable buffer for different applications. The buffer will be chosen based on the desired application, e.g., it may be a biological buffer compatible with body tissues and cells or it may be a chemical buffer compatible with use in chemical or nanotechnological applications. In one embodiment, the glue so produced could be employed in surgical procedures in the place of sutures. In yet another approach, the glue could be utilized to coat surfaces of biological traps for disinfestations purposes. Spider glue can also be utilized in nanotechnological applications for affixing micro- and nano-structures (such as DNA, protein fibers or threads, small molecules, films, spider silks etc.) to surfaces. Thus, the use of spider glue as a fixative where appropriate in also within the scope of the invention.

The spider glycoprotein glue described herein can also be utilized to seal an injection site created by, for example, a needle injection. Such a seal will increase the efficiency of the injected material's uptake since leaking and dispersion sometimes result from the removal of a needle, especially along the needle track. In such arrangements of the invention the spider glycoprotein glue can be added to the agent being injected prior to administration. Alternatively, the spider glycoprotein glue may be coated on the exterior of the needle prior to administration. In another arrangement, the spider glycoprotein glue is administered topically to the injection site after administration and removal. In any of the above cases, the spider glycoprotein glue results in an increase of affinity of the injected material into the tissue, and overall, such methods inhibit the leakage of the agent that has been injected into tissue.

The availability of the nucleic acids encoding the spider glue proteins of the invention also provides the means to genetically engineer protein based agents in vectors to produce a fusion protein of the protein based agent and the spider glue component. For treatment of bone disorders, such as fractures or bone cancer, the spider glue protein may be fused to a protein which stimulates bone growth, (e.g., bone morphogenic protein) and administered to the lesion to augment or enhance bone healing. In an alternative approach, the spider glue proteins can be chemically modified (e.g., by cross-linking) to include a bioactive substance for delivery to the desired target site. Such in vivo uses such as these are described hereinafter.

III. BIOACTIVE AGENTS CONTAINED IN SPIDER GLYCOPROTEIN GLUE AS BIOLOGICAL CARRIER COMPOSITIONS

In certain approaches, it may be desirable to utilize liposome formulations or spider glycoprotein-nanoparticle formulations. The basic constituents of liposomes are various saturated or unsaturated lipids or phospholipids, with or without the addition of cholesterol and other constituents, such as aliphatic compounds having either amino or carboxylic acid groups. Liposomes of several types suitable for use in the present invention may be prepared by a variety of techniques that may ultimately influence liposome morphology, type, and size. Many techniques for preparing liposomes have been described (Szoka Jr. and Papahaddjopoulos, D. (1980), Ann. Rev. Biophys. Bioengineering, 9:467-508; Gregorius G. (Ed). (1983) Liposome Technology, Vols. I, II, III., CRC Press, Boca Raton, Fla. (1991); Ostro (Ed)., Liposome Preparations: Methods & Mechanisms, Marcel Dekker Inc. NY; Davis, S. S. and Walker, I. M., (1987), Methods in Enzymology 149: 51-64). These methods are applicable for producing liposomes for embedding into the spider glycoprotein glue to be applied to a specific tissue site. As one example, a technique for producing liposomes for use in the invention is by ethanol injection. In this technique, equimolar quantities of cholesterol and hydrogenated lecithin are mixed and warmed to 60° C. in ethanol to form a solution, and the solution is injected in an aqueous buffer at 60° C. containing the material to be encapsulated. The emulsion is incubated 60° C. for one hour, centrifuged at 2000×g for 5 minutes, and the supernatant is removed. The liposomes are suspended in Tris-saline buffer and stored at 4° C.

Liposomes of several types are suitable for use in the present invention. For example, neutral liposomes are formulated with equimolar amounts of cholesterol and hydrogenated lecithin and are referred to as neutral liposomes. Other compositions of liposomes are formulated with 50% cholesterol, 40% hydrogenated lecithin, and 10% stearyl amine on a molar basis. As a consequence of their composition, these liposomes have free amine groups on their surfaces which are potentially capable of affecting certain biophysical parameters of the spider glycoprotein glue composition. Yet another type of liposomes are formulated with 50% cholesterol, 40% hydrogenated lecithin, and 10% stearic acid on a molar basis. Finally, liposomes can be formulated with 50% cholesterol, 40% hydrogenated lecithin, and 10% diethylstearylamine on a molar basis. Depending on pH, exemplary liposomes may contain electrically-charged chemical moieties on their surfaces.

The spider glycoprotein glue/liposome or nanoparticle compositions of the invention are designed to contain, carry, and release biologically active agents in accordance with the internal load or capacity of the liposomes. Liposomes or nanoparticles containing biologically active substances (i.e., medicaments) are embedded in the spider glycoprotein glue and will carry and release their contents at a wound site or surgical or nonsurgical opening in animals, including humans, to aid in the healing and protection process following all types of surgical or wound healing procedures. Examples of applications for the "loaded" liposomes or nanoparticles in spider glycoprotein glue include, but are not limited to, partial or complete replacement of sutures in skin grafts, burns or ulcers, or surgical and nonsurgical openings; nerve and vessel anastomoses; surgery of soft tissues, such as parenchymal tissues of liver, lung, or spleen; microsurgeries in all areas of the body; orthopedic surgeries for tendon repair and bone or cartilage grafting, general surgeries, such as cuts and laceration repair; cardiovascular surgery for vascular grafts and anastomoses; thoracic surgery to seal duct leaks and esophageal anastomoses; otolaryngology-head and neck surgery; ophalmological surgeries, general dental use and surgeries; general surgeries in various anatomical body parts and sites.

A wide variety of biologically active agents as well as medicines and pharmaceuticals may be contained within the liposomes or nanoparticles of the spider glycoprotein glue formulation. Examples of various agents to be entrapped in the liposomes or nanoparticles include, but are not limited to, drugs, neuroleptics, vitamins (e.g. Vitamin C, (i.e. ascorbic acid or ascorbate), Vitamin A, Vitamin E, Vitamin D, Vitamin B, or derivatives thereof), growth factors (e.g. lymphokines, cytokines), hormones, steroids, glucocorticosteroids, antibiotics (e.g. penicillin, gentimycin, erythromycin, adriamycin, tobramycin), antibacterial compounds, including bacteriocidal and bacteriostatic compounds, antiviral compounds, antifungal compounds, antiparasitic compounds, tumoricidal compounds, tumoristatic compounds, toxins, enzymes, enzyme inhibitors, proteins, peptides, minerals (such as zinc or copper), neurotransmitters, lipoproteins, glycoproteins, immunomodulators, immunoglobulins and fragments thereof, dyes, radiolabels, radiopaque compounds, fluorescent compounds, fatty acid derivatives, polysaccharides, cell receptor binding molecules, anti-inflammatories, antiglaucomic compounds, mydriatic compounds, anesthetics, nucleic acids (e.g. RNA and DNA fragments), and polynucleotides. It is also envisioned that selected fragments, portions, derivatives, or analogues of some or all of the above may be used, when practical, as additives in the aqueous phase of the liposomes of the invention. In addition, lipophilic drugs or other compounds may be incorporated into the phospholipid membrane of the liposomes.

The invention is suitable for multiple bioactive agents to be contained in liposomes or nanoparticles used in the spider glycoprotein glue bioadhesive composition. Should such a utility be desired, two or more bioactive agents may be entrapped in one liposome type which forms an integral part of the spider glycoprotein glue, and becomes subsequently embedded or deposited in the glue clot. Alternatively, two or more different types of liposomes or mixtures of liposome populations, each of which entraps the same or different bioactive agents, may be embedded in the spider glycoprotein glue-liposome composition. Different preparations of liposomes may comprise monophasic lipid vesicles (i.e. those having unilamellar lipid bilayers) or plurilamellar vesicles (i.e. those having multilamellar lipid bilayers), such as have been described previously (M. Schafer-Korting et al., 1989, J. Am. Acad. Dermatol., 21:1271-1275; U.S. Pat. No. 4,708,861 to M. C. Popsecu et al.). As envisioned for use in the present spider glycoprotein glue and liposome composition, one type of liposome (e.g. neutral liposomes) is formulated to entrap a particular bioactive material and a second type of liposome (either the same type as the first or a different type) is formulated to entrap another bioactive material. Both types of liposomes containing their respective bioactive contents are mixed with the components comprising fibrin glue, and the resulting spider glycoprotein glue and liposome composition contains two types of liposomes capable of delivering their respective bioactive contents at the incision or wound or opening site. This glue can be used for repairing tissue, for example, bronchial fistulas, corneal grafts, and dura tears, among other applications. It is apparent that mixtures of different types of liposomes containing a variety of bioactive materials may be formulated and embedded in the composition.

As one of skill in the art will appreciate, a nanoparticle in accordance with the methods and compositions of the present invention can be composed of a variety of injectable biodegradable polymers. Nanoparticles are said to be biodegradable if the polymer of the nanoparticle dissolves or degrades within a period that is acceptable in the desired application (usually in vivo therapy), usually less than five years, and desirably less than one year, upon exposure to a physiological solution of pH 6-8 having a temperature of between 25° C. and 37° C. As such, a nanoparticle for use in accordance with the methods and compositions of the present invention can be composed of homopolymers or copolymers prepared from monomers of polymers, wherein the copolymer can be of diblock, triblock, or multiblock structure as described in U.S. Patent Application 20060067925, which is incorporated by reference herein. Suitable polymers include, but are not limited to, poly(lactide-co-glycolides), poly(lactic acid), poly (alkylene glycol), polybutylcyanoacrylate, poly(methylmethacrylate-co-methacrylic acid), poly-allylamine, polyanhydride, polyhydroxybutyric acid, or polyorthoesters and the like. Particular combinations and ratios of polymers are well-known to the skilled artisan and any suitable combination can be used in the nanoparticle formulations of the present invention. Generally, the resulting nanoparticle typically ranges in size from between 1 nm and 1000 nm, or more desirably between 1 nm and 100 nm, and can be combined with the spider glycoprotein glue described herein.

An advantage of the spider glycoprotein glue of the invention is that it is physiologically compatible with biological systems for in vivo use, such that both it and the liposomes or nanoparticles contained therein, provide beneficial effects for the recipient animal without being toxic. Similarly, another advantage of the spider glycoprotein glue-liposome or nanoparticle compositions is that the liposome-glue or nanoparticle-glue will remain in clotted form in the environment in which it is administered or applied due to the formulations of present compositions of the invention, and will withstand physiological body temperatures and the conditions of the host environment in vivo. Because they comprise phospholipids and cholesterol, the liposomes of the composition will also be naturally metabolized over time by absorption by cells and tissue (reviewed by Schater-Korting M., Korting H C. and Braun-Falco, O. J., 1989, Amer. Acad. Dermatol. 21: 1271-1275). It is clear that the fibrin glue allows for controlled localization and the release of the contents of the embedded liposomes into the desired tissue site.

IV. IN VIVO AND OTHER USES OF SPIDER GLYCOPROTEIN GLUE-CONTAINING LIPOSOME COMPOSITIONS

The spider glycoprotein glue-liposome composition of the present invention may be used for immediate or sustained release of a biologically active substance or medicament both in vitro and in vivo. For in vivo use at a surgical or nonsurgical site, the spider glycoprotein glue-liposome composition may be formulated in the number of ways elucidated above. In brief, the spider glycoprotein glue components and liposomes, however they are pre-mixed, may be added together at or over the wound site at the desired time of use. Consequently, the spider glycoprotein glue-liposome bioadhesive is formed in situ following the admixture and administration of all of the components at the site. Administration is preferably topical and includes, but is not limited to, application on, at, around, or near areas such as eyes, skin, ears, or on afflictions such as wounds, burns, surgical and nonsurgical openings, fissures, ulcers, blisters, bone breaks, and the like. The present invention is particularly useful for such treatments in which the release over time of antibiotics or healing, prophylactic, or therapeutic medicaments would assist in the healing and recovery process. In addition, because the biochemical action of spider glycoprotein glue mimics a part of a normal biological process, the fibrin glue-liposome composition may be used to promote hemostasis by controlling hemorrhaging, to seal and bond tissue, and to support wound healing. Similarly, the fibrin glue-containing liposome composition may be topically administered at the site of burns in which the release of antimicrobials, cell growth factors, and/or medicaments is also of critical importance in the promotion and speed of the healing process.

Spider glycoprotein glue containing liposomes can be also be used to bind bone fragments. The bone-binding ability of the spider glycoprotein glue and liposome composition is very useful in bone reconstruction, as in plastic surgery or the repair of major bone breaks. For example, a bone fracture can be sealed with the spider glycoprotein glue and liposome composition so that the glue both seals the break and entraps and localizes the liposomes which are formulated to contain bone-specific growth factors. Upon slow dissolution of the spider glycoprotein glue at the site of the bone fracture, the liposomes release their entrapped growth factors and thus improve the rate and quality of the healing bone.

Spider glycoprotein glue containing liposomes can also be fabricated as a film or membrane. Such films or membranes are advantageous to cover large surface areas. In addition, the spider glycoprotein glue and liposome compositions can be employed to fabricate implantable devices which include not only films, but also foams or chunks of the congealed spider silk glycoprotein glue and liposome composition. The films and devices may be formed ex vivo by application as liquids or sprays for subsequent implantation or use in vivo after gelation.

In one arrangement of the invention, spider glycoprotein glue-containing liposome compositions may be also be used to coat devices, such as prosthetic devices, catheters, stents, valves, and the like, which would be temporarily inserted or permanently implanted into an animal or human patient. A common practice in use with stenting procedures is the use of stents for administration of pharmaceutical agents to treat restenosis and other bodily ailments through a lumen wall.

The following example is provided to illustrate certain embodiments of the invention. It is not intended to limit the invention in any way.

EXAMPLE I

Isolation and Characterization of Nucleic Acids Encoding Spider Web Glue

In this example, two newly discovered genes that encode two subunits of the glue-glycoprotein of the golden orb weaving spider *Nephila clavipes* are described. Both putative glycoprotein subunits have unique repetitive domains that are individually expressed from opposite strands of the same DNA sequence. The successful cloning of these glycoprotein genes allows large-scale production for the development of new bio-based glues for numerous purposes, as described herein.

The following materials and methods are provided to facilitate the practice of the present invention.
cDNA Construction and Gene Cloning Adult females of the golden orb weaving spider *Nephila clavipes* were collected in Florida and dissected to isolate their aggregate glands. Glands were immediately frozen in liquid nitrogen and kept in a −80° C. freezer until use. Intact messenger RNA (mRNA) was extracted from those glands, using Tri Reagent® (#TR118, MRC, OH, USA) and oligo-T Dynabeads (#610.05, Dynal Biotech ASA, Oslo, Norway). This mRNA was promptly used to construct a directional complementary deoxyribonucleic acid (cDNA) library, using ZAP Express® cDNA synthesis kit and ZAP Express® cDNA Gigapack® III Gold Cloning kit (#200403, #200451, Stratagene, Calif., USA). The cDNA library was mass-excised to produce pBK-CMV vectors that were transformed into *Escherichia coli* host strain cells (as described by manufacturer, Stratagene, Calif., USA). The library was then screened by colony lifting. Plasmids were extracted from randomly selected colonies (QIAprep, 27104, Qiagen, CA, USA) and inserts were sequenced. One clone was isolated at relatively high frequency. This clone showed two possible reading frames on opposite DNA strands that translated into two highly repetitive and potentially glycosylated proteins. Oligonucleotides were individually designed towards the C-terminus of each potential gene (reading frame), based on this clone. The oligonucleotides are 5'CAGAAGAAC-CCGAAACACCGAGTCCAGAAAC3' (SEQ ID NO:5) towards the 3 prime end of asg1 and 5'GTTTCTGGACTCG-GTGTTTCGGGTTCTTCTG3' (SEQ ID NO:6) towards the 3 prime end of asg2. The oligonucleotides were used as primers to clone the C-terminus of each putative gene by Rapid Amplification of cDNA Ends Polymerase Chain Reaction (RACE-PCR) utilizing the cDNA library as a DNA template and a vector primer adjacent to the C-terminus of the inserted clone. PCR was carried out in a thermal cycler (MyCycler, Bio-Rad). The reactions were performed in a volume of 50 μl PCR solution containing 2 μl of template, 10 pMol of each primer and 45 μl Platinum PCR® SuperMix (#11306, Invitrogen, CA, USA). The thermal cycler was programmed to 95° C. (5 min) followed by 35 cycles of 95° C. (15 sec), 55° C. (45 sec) and 72° C. (5 min) followed by 72° C. (30 min). RACE-PCR products were purified (QIAquick Gel Extraction kit, 28704, Qiagen, CA, USA) and served as DNA templates in a further nested-PCR, utilizing the same primers and same conditions used in RACE-PCR. This strategy helped to amplify gene specific fragments and to avoid low concentration undetectable DNA fragments. Certain nested-PCR products were subcloned and sequenced. The resulting products were visualized on 1% TAE-agarose gel, cleaned (QIAquick Gel Extraction kit, 28704, Qiagen, CA, USA), cloned into a pCR® 4-TOPO® vector (TOPO TA Cloning® kit for sequencing, #K4530-20, Invitrogen, CA, USA) and sequenced. New oligonucleotides were generated towards the N-terminus of each putative gene, based on the newly discovered C-terminus sequences. Those were used as primers for RACE-PCR and nested PCR as described above. One oligonucleotide, 5'GGTGTAGTTGTTGGTTCTTCCG3' (SEQ ID NO: 7), was designed to clone the 5 prime end of asg1. Two oligonucleotides, 5'CCACTAAACCTTCCATTAAG3' (SEQ ID NO: 8) and 5'CCTAACATCTTCCGGTAATTCATCG3' (SEQ ID NO: 9), were designed to clone the 5 prime end of asg2. All samples were sequenced at the University of Wyoming sequencing facility. Sequence analysis was carried out using NCBI-BLAST (located on the Internet at: blast.ncbi.nlm.nih.gov/Blast.cgi) and EXPASY tools (located on the Internet at: ca.expasy.org/tools/).
Northern Blots The oligonucleotides that were designed towards the C-terminus of each gene (complementary to asg1 & complementary to asg2), were DIG-labelled (DIG Oligonucleotide 3'—end labelling kit, $2^{nd}$ generation, #03353575910, Roche Applied Science, IN, USA) and used as probes in northern blot analysis, utilizing total RNA and mRNA that were purified from different spider silk glands and tissues of *N. clavipes* (using intact glands and RNA extraction methods as described above). Northern blots were carried out according to DIG manufacturer protocols and reagents (Roche Applied Science, IN, USA). Specific reagents used: 2% agarose gel in 1×MOPS Buffer containing 2% formaldehyde, positively charged nylon membranes (#11209272001), hybridization solution 'DIG Easy Hyb' (#1603558), DIG wash and block buffer set (#11585762001), Anti-Digoxigenin-AP Fab fragments (#11093274910), CDP-Star (#11685627001).
Biochemical Analysis of Glycoprotein Uncontaminated fresh orb webs were obtained by maintaining spiders individually in cages for up to 8 months. Webs were collected daily on sterile glass rods and stored at −20° C. until analyzed. Each extraction included 60-70 webs. Collected rods coated with webs were ground by mortar and pestle and incubated in minimal volume of extraction buffer (6M guanidine HCl, 0.7M β-mercaptoethanol, 0.2M $Na_2HPO_4$) with protease inhibitor cocktail (#P2714, Sigma, Mo., USA) for 24 hours at 4° C. with gentle agitation.

Extracts were then centrifuged for 30 minutes at 4000 rpm (J-6M, Beckman Coulter, Germany). Supernatants were recentrifuged for 5 minutes at full speed (Microfuge18, Beckman Coulter, Germany) to discard insoluble web contents. Protein extraction samples dissolved in sample buffer (without β-mercaptoethanol), boiled for 10 minutes were resolved on 12% mini-SDS-PAGE. Approximately 200 μl were loaded per well in a concentration of 0.15 μg/μl. Gels were run for 5 hours at 60 volt in Tris-Glycine buffer with 0.01 M of Sodium thioglycolate. The gels were stained with glycoprotein-specific staining techniques (Pro-Q® Emerald 300, Molecular Probes, OR, USA). Gels were also stained using total protein stains such as SYPRO®Ruby (Molecular Probes, OR, USA) to assure the purity of the glycoprotein band. Positive bands (glycoprotein-specifically stained) were cut out from the gel and homogenized in 20% acetonitrile. Samples were then vortexed for 15 minutes, and acetonitrile was added to 50% of the solution. Samples were centrifuged for 5 minutes and the supernatants were collected. The gel pellet was subjected to 3-4 cycles of extraction as described above (supernatants were combined). Gel purified glycoprotein solution was dialyzed against double distilled water at 4° C., for 18 hours then lyophilized, re-suspended in 0.75% Triton X-100, 0.4% β-mercaptoethanol, 0.1% SDS and homogenized ultrasonically using a frequency of 20 KHz/Sec. for 5 minutes (Sonicator 3000, Misonix, N.Y., USA) upon ice. Samples were boiled for 15 minutes before being subjected to deglycosylation.

Protocols for the deglycosylation of purified glycoprotein solutions have been developed and adapted to glycoprotein from spider silk. Glycoprotein solutions, purified from SDS-PAGE bands, were used for deglycosylation. Protocols include enzymatic analyses based on E-DEGLY and PP0200 deglycosylation kits (Sigma, Mo., USA) which contain the N-linked glycoproteins cleavage enzyme PNGase F and the O-linked glycoproteins cleavage enzymes Endo-O-Glycosidase, α-2(3,6,8.9)-Neuraminidase (Sialidase A), β-1,4-Galactosidase and β-N-Acetylglucosaminidase. Approximately 100 μg of gel extracted glycoprotein were used in each reaction. Enzymes were directly added to the solution and the reaction was incubated for 24 hours at 37° C. Sample of deglycosylation reactions were then resolved on 12% mini-SDS-PAGE. The gels were stained with glycoprotein-specific staining techniques as described above. Gels were also stained by total protein stain. Differential and distinct bands stained by total protein staining were cut out from the gel and the glycoprotein was then extracted from the gel as described above. Gel purified glycoprotein solution was dialyzed and lyophilized (as described above). Proteins were subjected to trypsin digestion. Samples were then analyzed by mass spectrometry carried out by Thermo Electron Corporation (San Jose, Calif., USA) to obtain peptide sequences.

Results

Figure 2:
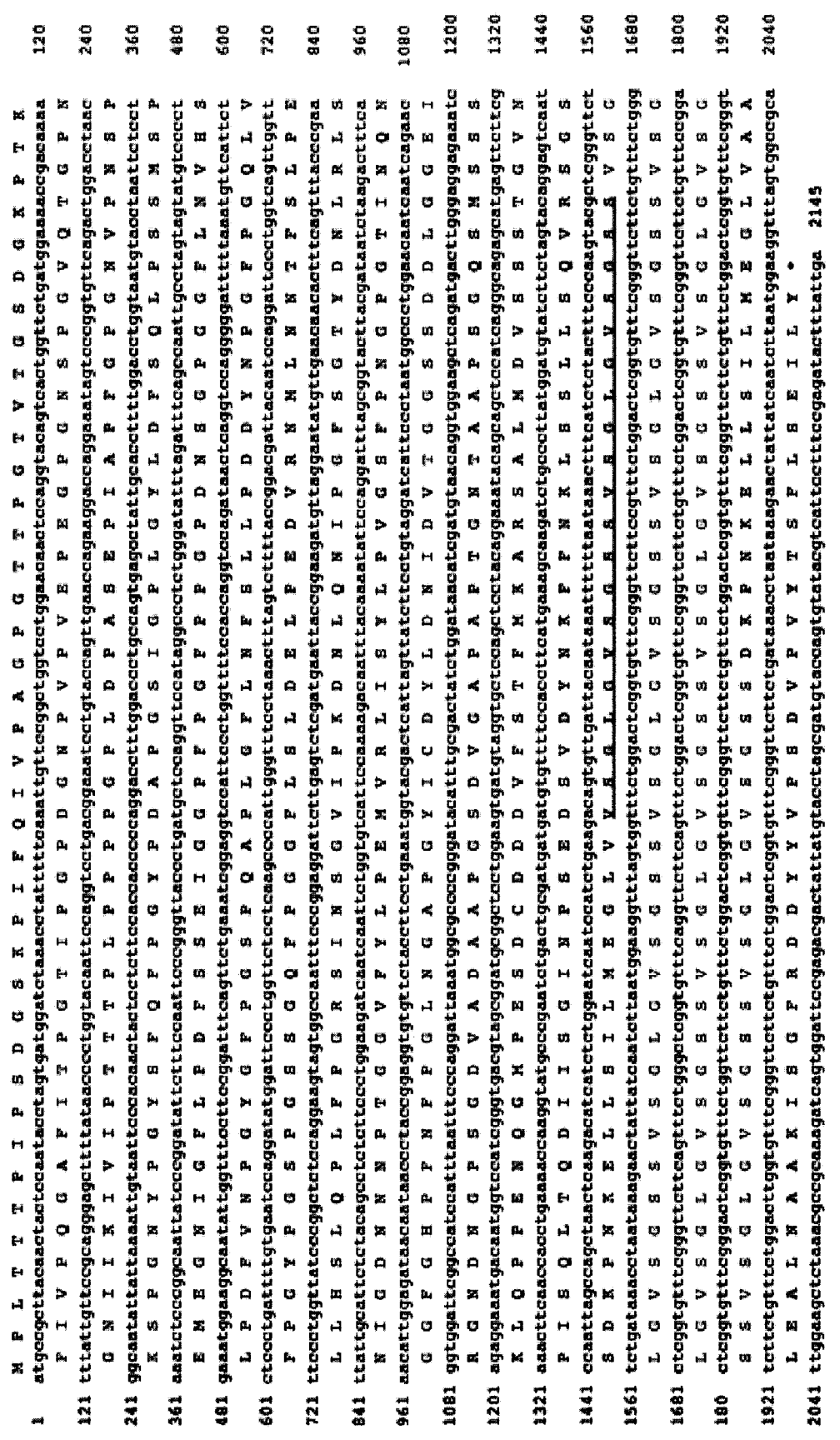

As a first step toward a molecular characterization of the glycoprotein from spider silk sticky coat, a *N. clavipes* aggregate gland complementary DNA (cDNA) library was constructed and screened. A frequently occurring DNA clone encoding a previously unknown repetitive and potentially glycosylated protein domain was discovered. In addition, this clone had an open reading frame on the opposite strand of the same DNA that could encode another previously unknown spider protein. Oligonucleotides based on each DNA strand were used in Rapid Amplification of cDNA Ends Polymerase Chain Reaction (RACE-PCR) to determine whether both putative proteins were indeed expressed in the aggregate gland tissue and if their full length clone existed in the cDNA library. As shown in FIGS. 1 and 2, two complete genes named Aggregate Spider Glue (asg1, asg2) were cloned that encode two different potentially glycosylated proteins (ASG1 and ASG2, respectively). Both proteins have multiple high potential O-glycosylation sites and one possible N-glycosylation site.

Each protein has a unique repetitive domain of eleven 10-amino acid repeats. Predictably, both proteins share the same highly repetitive 351-bp DNA that encodes their repetitive protein domains on opposite strands (FIG. 3).

Using northern blot analysis, the expression of asg1 and asg2 was tested in the aggregate glands, other silk glands such as major ampullate, minor ampullate, flagelliform, tubiliform and in messenger RNA (mRNA) extracts from the spider's body. Results revealed that both asg1 and asg2 mRNAs were exclusively expressed in the aggregate glands and were not detected in other spider glands or tissues. One probe detected an mRNA of 1.2-kb (FIG. 4*a*) and the other detected an mRNA of 2.2 kb (FIG. 4*b*).

Figure 5:
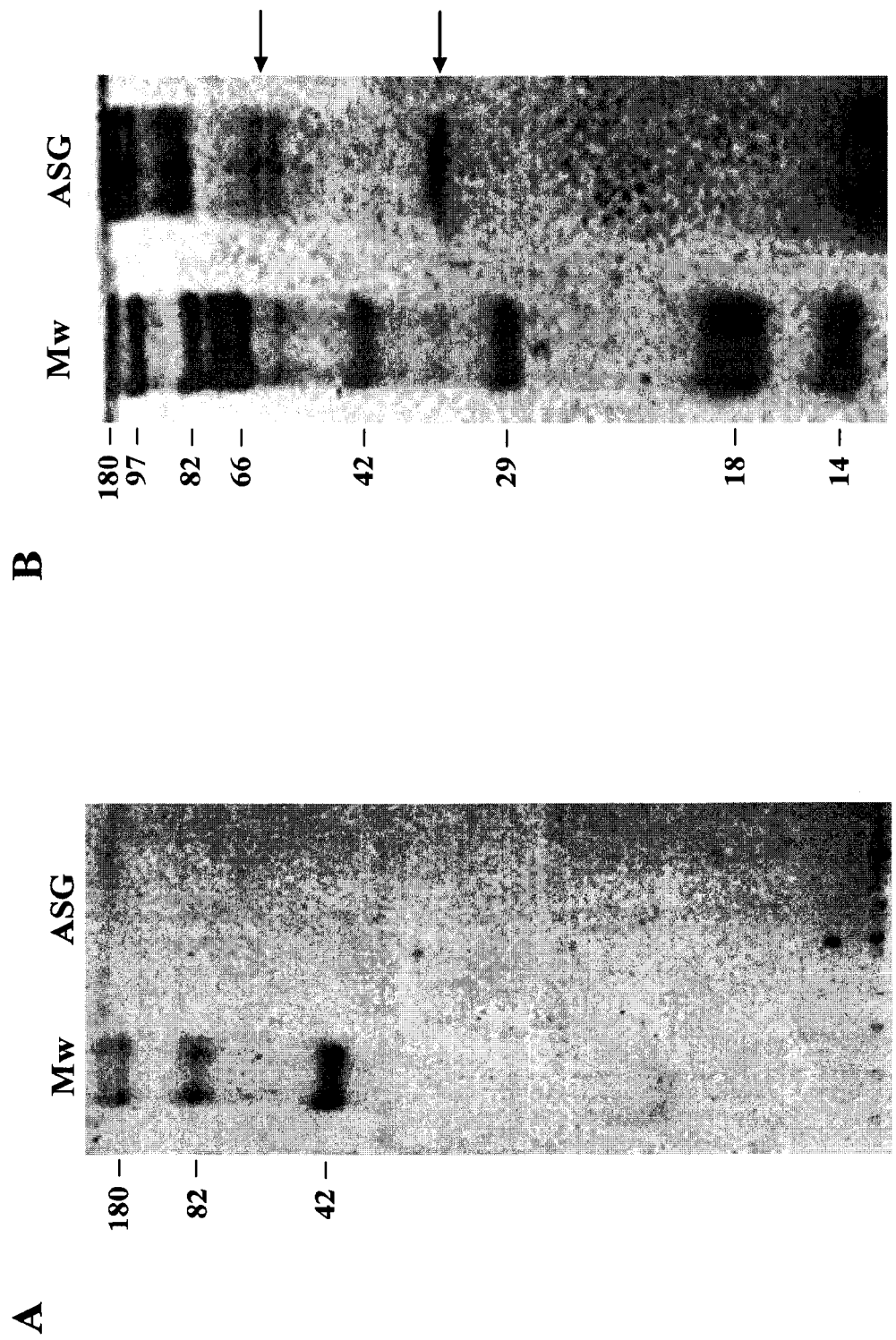
FIG. 5 is a 12% SDS-PAGE showing results of deglycosylation of the spider's glycoprotein purified from orb webs. Mw: Molecular weight marker indicating sizes in kDa (CandyCane™, Molecular Probes, OR, USA), ASG: deglycosylated spider's glycoprotein.

In these biochemical studies, a glycoprotein directly from spider orb webs was extracted and purified. Using specific glycoprotein detection methods, this protein was found to be the only glycoprotein associated with the aqueous coat of spider silk. This purified glycoprotein was deglycosylated and subjected to SDS-PAGE, which showed two bands of approximate sizes of 65 kDa and 38 kDa (FIG. 5).

Staining with highly specific glycoprotein stain clearly shows that no glycoprotein band can be detected at this stage, which indicates that no glycosylated glycoprotein remained in the solution after the enzymatic deglycosylation. Staining with total protein dye shows the two deglycosylated glycoprotein bands. Higher molecular weight bands on the gel were shown to be remains of the deglycosylation enzymes in the solution that were loaded on the gel and are not related to any of the spider's proteins. Additionally, the larger protein (subunit) was subjected to mass spectrometry analysis. Peptides derived from this analysis show identities to the translated protein ASG2. Two of the peptides found were Gly-Ser-Ser-Val-Ser (SEQ ID NO: 10) and Gly-Leu-Gly-Val (SEQ ID NO: 11), which appear as one repeating sequence (GSSVS-GLGV) (SEQ ID NO: 12) in ASG2 and Ala-Gly-Pro-Gly-Thr (SEQ ID NO: 13) also appears in ASG2.

Subsequently, spider glue glycoproteins in another orb-weaving spider, *Araneus gemmoides*, were searched, and a portion of the repetitive domain from this species was cloned. Comparison of sequences from both species shows 92% identity for ASG1 and 91% identity for ASG2. As shown in FIG. 6, both ASG1 and ASG2 from *N. clavipes* have an insert of five amino acids that does not appear in *A. gemmoides*.

Discussion

In accordance with the present invention, the molecular properties of two glycoproteins in the glue that coats the spiral capture prey threads of orb weaving spiders has been elucidated. These two glycoprotein subunits function as key components of the spider glue. The fact that both asg1 and asg2 mRNAs were exclusively expressed in the aggregate glands and were not detected in other spider glands or tissues shows that ASG1 and ASG2 are not products of housekeeping genes and are involved only in the function of the aggregate glands. Moreover, one probe detected an mRNA of 1.2-kb as expected from the size of the cloned DNA of asg1 (FIG. 1) and the other detected an mRNA of 2.2 kb as also expected from the size of cloned asg2 (FIG. 2). Since asg1 and asg2 share the same repetitive DNA sequence (FIG. 3) and the mRNA transcript of one is partially anti-sense to the transcript of the other and could prevent its translation, it appears that there is a separation by time or space of their expression. Further sequence analysis shows no additional sequence homologies between the two proteins. In addition both the N-terminal and C-terminal sequences of both proteins show no relevant homology to the highly conserved N- and C-termini of spider silk proteins.

Furthermore, deglycosylation of the only glycoprotein identified and purified from spider webs and biochemical analysis of the deglycosylation products demonstrates that the spider glue glycoprotein indeed functions as a combination of two subunits with approximate sizes (38 and 65 kDa) predicted from the size of the deduced ASG1 and ASG2 sequences (FIGS. 1 and 2). Peptide sequences derived from the 65 kDa deglycosylation product, originally derived from the spider web purified glycoprotein, show full identities to the translated protein ASG2. These results indicate that ASG2 functions as a key component in the spider web glue. Additionally, glycoproteins that were extracted and deglycosylated from two other species of orb weaving spiders, *A. gemmoides* and *Argiope trifasciata* showed the same pattern of two distinct bands of similar molecular weights as shown in FIG. 5, which further indicates that the spider glue nodules are made of two different glycoproteins.

Additionally, ASG1 appears to be highly glycosylated (25 O-glycosylation and 1 N-glycosylation sites, FIG. 1) and its repetitive domain shows sequence similarities to mucin repetitive domains, which are known to be highly glycosylated (6). This protein has a high proportion of charged amino acids in the nonrepetitive region which could aid in retention of water as is seen in the web droplets. The ASG2 repetitive domain shows similarities with elastin and flagelliform spider silk protein repetitive sequence domains, and its N-terminal region sequence is similar to other structural proteins such as collagen. In particular, it possesses a very high proportion of proline. It appears, based on structure-function analysis, that ASG2, when functioning as an oligomer, possesses some level of elasticity. ASG2 also appears to be glycosylated (16 O-glycosylation and 1 N-glycosylation sites, FIG. 2). Both traits are expected from the spider's sticky-coat-glycoprotein to act as glue. Highly glycosylated proteins, such as mucins are known to have adhesive traits (6) whereas the elasticity would help in the creation of expanding nodules as previously described for the spider's glycoprotein (5). In addition, the upstream nonrepetitive sequence of the ASG1 protein shows substantial similarities to chitin-binding proteins (25-30% identity, 50-55% similarity), which shows that this protein also has chitin binding traits that would be highly useful in its function of retaining insects in the web.

The glycoproteins of the spider glue are O-glycosylated (FIGS. 1 & 2) as previously described, and this is consistent with the biochemical analysis of the proteins from the web that match the identified cDNAs. Tillinghast et al. (4) purified and studied a glycoprotein from orb webs of the spider *Argiope aurantia* and studied its morphology and biochemical traits. Those investigators found that it has an apparent high molecular weight (>200 kDa) and has a residue of N-acetylgalactosamine O-linked to threonine. They also showed that the glycoprotein shares several characteristics with mammalian secretory mucins, and their electron microscopic examination of the glycoprotein preparation revealed poly-disperse linear macromolecules exhibiting considerable flexibility.

Although it has been previously shown in other species that opposite strands of the same DNA can encode for two independent proteins (7-8), it has never been described for highly repetitive domains in two proteins assumed to be functionally dependent as described herein. Furthermore, ASG2 shows similarities to flagelliform spider silk. Evolutionarily it is known that the aggregate glands and their contents evolved later than other silk glands and spider silk proteins (3). This shows that the repetitive glue DNA originally was derived from a spider silk gene and has evolved to its current form via gene duplication. The RNAs transcribed from each DNA strand then independently led to the evolution of two genes expressed in the aggregate glands, both involved in the generation of glycoprotein nodules that function as glue. Moreover, partial repetitive domains of asg1 and asg2 have been cloned from another orb weaving spider, *A. gemmoides*. This species evolutionarily separated from *N. clavipes* 125 million years ago, yet the repetitive domains of ASG1 and ASG2 from both species show 91-92% identity (FIG. 6).

*N. clavipes* domains have an insert of five amino acids that do not exist in *A. gemmoides* genes, which shows that the original DNA of the genes had already existed in the their ancestor's genome and mutation in the DNA independently appeared in *N. clavipes* after separation of species. Despite this mutation, the high similarities of the current proteins between species shows that they are highly important for the survival of orb weaver spiders, in functioning as glue, necessary to retain prey in the web.

The fact that both species examined have maintained the identity of these sequences in the two genes despite more than 100 million years of separation indicates its importance. This is particularly true because the five amino acid insertion or deletion between the two species is seen in both genes, respectively.

The results presented herein, together with comparisons to previous studies of the putative spider glue glycoprotein, contribute novel biological and evolutionary knowledge of these specific genes and their partner proteins. Over-expression of the cloned genes in systems such as insect or bacterial cell cultures will facilitate large-scale production of the glycoprotein that can be used to develop new bio-based glues to serve medical, military, or other commercial purposes.

REFERENCES

1. Lewis R-V (2006) Spider silk: ancient ideas for new biomaterials. *Chem Rev* 106: 3762-3774.
2. Peters H-M (1995) Ultrastructure of orb spiders' gluey capture threads. *Naturwissenschaften* 82: 380-382.
3. Vollrath F, Fairbrother W-J, Williams R-J-P, Tillinghast E-K, Bernstein D-T, Gallagher K-S, Townley M-A (1990) Compounds in the droplets of the orb spider's viscid spiral. *Nature* 345: 526-527.
4. Tillinghast, E-K, Townley M-A, Wight T-N, Uhlenbruck G, Janssen E (1993) The adhesive glycoprotein of the orb web of *Ariope aurantia* (Araneae, Araneidae). *Mater Res Soc Symp Proc* 292: 9-23.
5. Vollrath F, Tillinghast E-K (1991) Glycoprotein glue beneath a spider web's aqueous coat. *Naturwissenschaften* 78: 557-559.
6. Beeley J G in *Glycoprotein and Proteoglycan Techniques*, eds Burdon R H and van Knippenberg (Elsevier Amsterdam-New York-Oxford, 1985), Vol. 16.
7. Adelman P (1987) Two mammalian genes transcribed from opposite strands of the same DNA locus. *Science* 235: 1514-1517.
8. Shintani, S, O'hUigin C, Toyosawa S, Michalová V, Klein J (1999) Origin of gene overlapping: the case of TCP1 and ACAT2. *Genetics* 152: 743-754.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. An isolated polynucleotide encoding a protein of SEQ ID NO: 2.

2. The polynucleotide of claim 1 which is SEQ ID NO: 1.

3. An isolated polynucleotide encoding a protein of SEQ ID NO: 4.

4. The polynucleotide of claim 3 which is SEQ ID NO: 3.

5. An isolated glycoprotein of SEQ ID NO: 2.

6. An isolated glycoprotein of SEQ ID NO: 4.

7. A biological glue comprising a complex of SEQ ID NO: 2 of claim 1 and SEQ ID NO: 4 of claim 2.

8. A pharmaceutical composition comprising the glycoproteins of claims 5 and 6 in a pharmaceutically acceptable carrier for administration to an individual.

9. A method for producing a glycoprotein glue for use as a wound sealant comprising, providing the composition of claim 8, wherein said composition is capable of sealing a wound.

10. The method of claim 9, wherein said sealant is combined with a biological carrier.

11. The method of claim 9, wherein said sealant is combined with a chemical carrier.

12. A method for producing a liposome-containing, glycoprotein glue, comprising:
   a) providing the composition of claim 8;
   b) liposomes containing at least one therapeutic agent entrapped therein; and
   c) mixing the composition of a) and the liposomes of b) to form a liposome-containing, glycoprotein glue in which said liposomes are entrapped for delivery to an individual.

13. The method according to claim 12, wherein step c) occurs at a wound site caused by injury or in a lumen within an individual.

14. The method according to claim 12, wherein said liposome entrapped medicament is selected from the group consisting of neuroleptics, vitamins, growth factors, steroids, antibiotics, narcotics, antibacterial compounds, bacteriocidal compounds, bacteriostatic compounds, antiviral compounds, antifungal compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids, and polynucleotides.

15. The method according to claim 13, wherein said liposome entrapped medicament is selected from the group consisting of neuroleptics, vitamins, growth factors, steroids, antibiotics, narcotics, antibacterial compounds, bacteriocidal compounds, bacteriostatic compounds, antiviral compounds, antifungal compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids, and polynucleotides.

16. A method of treating a lumen with a therapeutic agent, comprising applying the composition of claim 8 within said lumen, said composition containing at least one liposome with at least one therapeutic agent entrapped therein.

* * * * *

SEQUENCE LISTING

<160> NUMBER OF SEQ ID NOS: 13

<210> SEQ ID NO 1
<211> LENGTH: 1221
<212> TYPE: DNA
<213> ORGANISM: Nephila clavipes

<400> SEQUENCE: 1

| | | | | | |
|---|---|---|---|---|---|
| atgtatacac | attattttag | cattttata | gtcatcttta | cagctactt | gattggtgta | 60 |
| gaaagtacgg | gtaaaactga | tgacagcagc | acaaatgaag | tacaaaacat | cgttatagag | 120 |
| aatggatcca | gaggttggcc | atgggacaaa | gaaaatcca | attttgtctg | cccttacct | 180 |
| tttggggtgt | ttctgatgt | aacagattgc | tctcgttttt | acctttgtgt | cgcgggtgta | 240 |
| gccagtcgca | aaaatgcca | gcgtgcgcag | cagtttgata | aatatagaaa | gaaatgtttg | 300 |
| ccctttatta | ttgctgtatg | tgacaaaggt | gacgatggtt | cttcttcaac | agccccaacg | 360 |
| actacaacaa | aaaagatgg | cgacgacgag | aaattacat | gcccaagtct | tattggttg | 420 |
| ttcatgcatc | ccaaagactg | ctcaaaatat | tattcttgca | cccttatat | accaaccttg | 480 |
| aagtcgtgtc | ctgacctgca | attatttgat | ggtgtcaagt | tgtcttgtaa | accagcgaaa | 540 |
| gatgttcatt | gtggaaaccg | aaaaagacca | gatgaattaa | ctactcctga | tgaaacaaca | 600 |
| gcagaaatta | tacctactga | agaacccgaa | acaccgagtc | cagaaacaga | agaacccgaa | 660 |
| acaccaagtc | cagaaacaga | agaacccgaa | acaccgagtc | cagaaacaga | agaacccgaa | 720 |
| acaccgagtc | cagaaacaga | agaacccgaa | acaccgagtc | cagaaacaga | agaaccagaa | 780 |
| acaccgagtc | ccgaaacacc | gagtccggaa | acagaagaac | ccgaaacacc | gagtccagaa | 840 |
| acagaagaac | ccgaaacacc | gagtccagaa | actgaagaac | ctgaaacacc | gagcccagaa | 900 |
| actgaagaac | ccgaaacacc | gagcccagaa | acagaagaac | ccgaaacacc | gagtccagaa | 960 |
| acggaagaac | caacaactac | accaaaaccc | cgtgtaacag | ctccagaaac | agattgtgat | 1020 |
| gaaaatgatg | tagattgcat | catcgacgat | ttgggaataa | ccctgactg | gttcaaatgt | 1080 |
| cctgaagata | taggaagtta | tcctcaccca | agtagcaaaa | aattattcat | cttttgcctc | 1140 |
| aactggaagc | catcggtgaa | aaagtgcgga | caagattga | tattttctga | ggaactgatg | 1200 |
| gcatgtgatc | gaccttatta | g | | | | 1221 |

<210> SEQ ID NO 2
<211> LENGTH: 406
<212> TYPE: PRT
<213> ORGANISM: Nephila clavipes

<400> SEQUENCE: 2

Met Tyr Thr His Tyr Phe Ser Ile Phe Ile Val Ile Phe Thr Ala Thr
1               5                   10                  15

Leu Ile Gly Val Glu Ser Thr Gly Lys Thr Asp Asp Ser Ser Thr Asn
            20                  25                  30

Glu Val Gln Asn Ile Val Ile Glu Asn Gly Ser Arg Gly Trp Pro Trp
        35                  40                  45

Asp Lys Glu Lys Ser Asn Phe Val Cys Pro Leu Pro Phe Gly Val Phe
    50                  55                  60

Ser Asp Val Thr Asp Cys Ser Arg Phe Tyr Leu Cys Val Ala Gly Val

|   | 65 |   |   |   | 70 |   |   |   | 75 |   |   |   | 80 |
|---|----|---|---|---|----|---|---|---|----|---|---|---|----|

Ala Ser Arg Lys Lys Cys Gln Arg Ala Gln Gln Phe Asp Lys Tyr Arg
             85            90            95

Lys Lys Cys Leu Pro Phe Ile Ile Ala Val Cys Asp Lys Gly Asp Asp
      100             105            110

Gly Ser Ser Thr Ala Pro Thr Thr Thr Lys Lys Asp Gly Asp
     115            120           125

Asp Glu Lys Phe Thr Cys Pro Ser Leu Ile Gly Leu Phe Met His Pro
130             135            140

Lys Asp Cys Ser Lys Tyr Tyr Ser Cys Thr Leu Tyr Ile Pro Thr Leu
145           150           155           160

Lys Ser Cys Pro Asp Leu Gln Leu Phe Asp Gly Val Lys Leu Ser Cys
      165             170            175

Lys Pro Ala Lys Asp Val His Cys Gly Asn Arg Lys Arg Pro Asp Glu
        180           185           190

Leu Thr Thr Pro Asp Glu Thr Thr Ala Glu Ile Ile Pro Thr Glu Glu
         195           200           205

Pro Glu Thr Pro Ser Pro Glu Thr Glu Glu Pro Glu Thr Pro Ser Pro
210             215            220

Glu Thr Glu Glu Pro Glu Thr Pro Ser Pro Glu Thr Glu Glu Pro Glu
225             230            235           240

Thr Pro Ser Pro Glu Thr Glu Glu Pro Glu Thr Pro Ser Pro Glu Thr
        245           250           255

Glu Glu Pro Glu Thr Pro Ser Pro Glu Thr Pro Ser Pro Glu Thr Glu
      260             265           270

Glu Pro Glu Thr Pro Ser Pro Glu Thr Glu Pro Glu Thr Pro Ser
     275            280           285

Pro Glu Thr Glu Glu Pro Glu Thr Pro Ser Pro Glu Thr Glu Glu Pro
        290           295           300

Glu Thr Pro Ser Pro Glu Thr Glu Glu Pro Glu Thr Pro Ser Pro Glu
305             310            315           320

Thr Glu Glu Pro Thr Thr Thr Pro Lys Pro Arg Val Thr Ala Pro Glu
        325           330           335

Thr Asp Cys Asp Glu Asn Asp Val Asp Cys Ile Ile Asp Asp Leu Gly
      340             345           350

Ile Thr Pro Asp Trp Phe Lys Cys Pro Glu Asp Ile Gly Ser Tyr Pro
        355           360           365

His Pro Ser Ser Lys Lys Leu Phe Ile Phe Cys Leu Asn Trp Lys Pro
     370            375           380

Ser Val Lys Lys Cys Gly Gln Asp Leu Ile Phe Ser Glu Glu Leu Met
385             390            395           400

Ala Cys Asp Arg Pro Tyr
        405

<210> SEQ ID NO 3
<211> LENGTH: 2145
<212> TYPE: DNA
<213> ORGANISM: Nephila clavipes

<400> SEQUENCE: 3

| atgccgctta | caactactcc | aatacctagt | gatggatcta | aacctatttt | tcaaattgtt | 60 |
| ccggctggtc | ctggaacaac | tccaggtaca | gtcactggtt | ctgatggaaa | accgacaaaa | 120 |
| tttattgttc | cgcagggagc | ttttataacc | cctggtacaa | ttccaggtcc | tgacggaaat | 180 |
| cctgtaccag | ttgaaccaga | aggaccagga | aatagtcccg | tgttcagac | tggacctaac | 240 |

```
ggcaatatta ttaaaattgt aattcccaca actactcctc ttccaccacc cccaggacct    300
ttggaccctg ccagtgagcc tattgcacct tttggacctg gtaatgtacc taattctcct    360
aaatctcccg gcaattatcc cggatatcct ttccaattcc cgggttaccc tgatgctcca    420
ggttccatag gccctctggg atatttagat ttcagccaat gcctagtag tatgtcccct     480 gaaatggaag gcaatattgg tttccttccg gatttcagtt ctgaaatcgg aggtccattc    540
cctggttttc caccaggtcc agataactca ggtccagggg gattttttaaa tgttcattct   600 ctccctgatt ttgtgaatcc aggatatgga ttccctggtt ctcctcaagc cccattgggt   660
ttcctaaact ttagtctttt accggacgat tacaatccag gattccctgg tcagttggtt   720
ttccctggtt atcccggctc tccaggaagt agtggccaat tcccggagg attcttgagt    780 ctcgatgaat taccggaaga tgttaggaat atgttgaaca cactttcag tttacccgaa    840 ttattgcatt ctctacagcc tctcttccct ggaagatcaa tcaattctgg tgtcattcca    900
aaagacaatt tacaaaatat tccaggattt agcggtactt acgataatct aagactttca    960
aacattggag ataacaataa ccctaccgga ggtgtgttct accttcctga atggtacga   1020 ctcattagtt atcttcctgt aggatcattc cctaatggcc tggaacaat caatcagaac   1080 ggtggattcg ccatccatt taatttccca ggattaaatg gcgccccggg atacatttgc    1140
gactatctgg ataacatcga tgtaacaggt ggaagctcag atgacttggg aggagaaatc   1200
agaggaaatg acaatggtcc atcgggtgac gtagcggatg cggctcctgg aagtgatgta    1260
ggtgctccag ctcctacagg aaatacagca gctccatcag ggcagagcat gagttcttcg    1320
aaacttcaac cacctgaaaa ccaaggtatg cccgaatctg actgcgatga tgatgtgttt    1380
tccaccttca tgaaagcaag atctgccctt atggatgtat cttctagtac aggagtcaat    1440
ccaattagcc agctaactca agacatcatc tctggaatca atccatctga agacagtgtt    1500
gattacaata aattttttaa taaactttca tctctacttt cccaagtacg ctcgggttct   1560
tctgataaac ctaataaaga actattatca atcttaatgg aaggtttagt ggtttctgga    1620
ctcggtgttt cgggttcttc cgtttctgga ctcggtgttt cgggttcttc tgtttctggg    1680
ctcggtgttt cgggttcttc agtttctggg ctcggtgttt caggttcttc agtttctgga    1740
ctcggtgttt cgggttcttc tgtttctgga ctcggtgttt cgggttcttc tgttccgga    1800 ctcggtgttt cgggactcgg tgtttctggt tcttctgttt ctggactcgg tgtttcgggt    1860
tcttctgttt ctggactcgg tgtttcgggt tcttctgttt ctggactcgg tgtttcgggt    1920
tcttctgttt ctggacttgg tgtttcgggt tcttctgttt ctggactcgg tgtttcgggt    1980
tcttctgata aacctaataa agaactatta tcaatcttaa tggaaggttt agtggccgca    2040
ttggaagctc taaacgccgc aaagatcagt ggattccgag acgactatta tgtacctagc    2100
gatgtaccag tgtatacgtc attccttcc gagatacttt attga                    2145
```

<210> SEQ ID NO 4
<211> LENGTH: 714
<212> TYPE: PRT
<213> ORGANISM: Nephila clavipes

<400> SEQUENCE: 4

Met Pro Leu Thr Thr Thr Pro Ile Pro Ser Asp Gly Ser Lys Pro Ile
1               5                   10                  15

Phe Gln Ile Val Pro Ala Gly Pro Gly Thr Thr Pro Gly Thr Val Thr
            20                  25                  30

Gly Ser Asp Gly Lys Pro Thr Lys Phe Ile Val Pro Gln Gly Ala Phe

```
                35                  40                  45
Ile Thr Pro Gly Thr Ile Pro Gly Pro Asp Gly Asn Pro Val Pro Val
 50                  55                  60
Glu Pro Glu Gly Pro Gly Asn Ser Pro Val Gln Thr Gly Pro Asn
 65                  70                  75                  80
Gly Asn Ile Ile Lys Ile Val Ile Pro Thr Thr Pro Leu Pro Pro
                 85                  90                  95
Pro Pro Gly Pro Leu Asp Pro Ala Ser Glu Pro Ile Ala Pro Phe Gly
                100                 105                 110
Pro Gly Asn Val Pro Asn Ser Pro Lys Ser Pro Gly Asn Tyr Pro Gly
                115                 120                 125
Tyr Ser Phe Gln Phe Pro Gly Tyr Pro Asp Ala Pro Gly Ser Ile Gly
                130                 135                 140
Pro Leu Gly Tyr Leu Asp Phe Ser Gln Leu Pro Ser Ser Met Ser Pro
145                 150                 155                 160
Glu Met Glu Gly Asn Ile Gly Phe Leu Pro Asp Phe Ser Glu Ile
                165                 170                 175
Gly Gly Pro Phe Pro Gly Phe Pro Gly Pro Asp Asn Ser Gly Pro
                180                 185                 190
Gly Gly Phe Leu Asn Val His Ser Leu Pro Asp Phe Val Asn Pro Gly
                195                 200                 205
Tyr Gly Phe Pro Gly Ser Pro Gln Ala Pro Leu Gly Phe Leu Asn Phe
                210                 215                 220
Ser Leu Leu Pro Asp Asp Tyr Asn Pro Gly Phe Pro Gly Gln Leu Val
225                 230                 235                 240
Phe Pro Gly Tyr Pro Gly Ser Pro Gly Ser Ser Gly Gln Phe Pro Gly
                245                 250                 255
Gly Phe Leu Ser Leu Asp Glu Leu Pro Glu Asp Val Arg Asn Met Leu
                260                 265                 270
Asn Asn Thr Phe Ser Leu Pro Glu Leu Leu His Ser Leu Gln Pro Leu
                275                 280                 285
Phe Pro Gly Arg Ser Ile Asn Ser Gly Val Ile Pro Lys Asp Asn Leu
                290                 295                 300
Gln Asn Ile Pro Gly Phe Ser Gly Thr Tyr Asp Asn Leu Arg Leu Ser
305                 310                 315                 320
Asn Ile Gly Asp Asn Asn Pro Thr Gly Val Phe Tyr Leu Pro
                325                 330                 335
Glu Met Val Arg Leu Ile Ser Tyr Leu Pro Val Gly Ser Phe Pro Asn
                340                 345                 350
Gly Pro Gly Thr Ile Asn Gln Asn Gly Gly Phe Gly His Pro Phe Asn
                355                 360                 365
Phe Pro Gly Leu Asn Gly Ala Pro Gly Tyr Ile Cys Asp Tyr Leu Asp
                370                 375                 380
Asn Ile Asp Val Thr Gly Gly Ser Ser Asp Leu Gly Gly Glu Ile
385                 390                 395                 400
Arg Gly Asn Asp Asn Gly Pro Ser Gly Asp Val Ala Asp Ala Pro
                405                 410                 415
Gly Ser Asp Val Gly Ala Pro Ala Pro Thr Gly Asn Thr Ala Ala Pro
                420                 425                 430
Ser Gly Gln Ser Met Ser Ser Lys Leu Gln Pro Pro Glu Asn Gln
                435                 440                 445
Gly Met Pro Glu Ser Asp Cys Asp Asp Asp Val Phe Ser Thr Phe Met
                450                 455                 460
```

-continued

Lys Ala Arg Ser Ala Leu Met Asp Val Ser Ser Thr Gly Val Asn
465                 470                 475                 480

Pro Ile Ser Gln Leu Thr Gln Asp Ile Ile Ser Gly Ile Asn Pro Ser
            485                 490                 495

Glu Asp Ser Val Asp Tyr Asn Lys Phe Phe Asn Lys Leu Ser Ser Leu
        500                 505                 510

Leu Ser Gln Val Arg Ser Gly Ser Ser Asp Lys Pro Asn Lys Glu Leu
    515                 520                 525

Leu Ser Ile Leu Met Glu Gly Leu Val Val Ser Gly Leu Gly Val Ser
530                 535                 540

Gly Ser Ser Val Ser Gly Leu Gly Val Ser Gly Ser Ser Val Ser Gly
545                 550                 555                 560

Leu Gly Val Ser Gly Ser Ser Val Ser Gly Leu Gly Val Ser Gly Ser
            565                 570                 575

Ser Val Ser Gly Leu Gly Val Ser Gly Ser Ser Val Ser Gly Leu Gly
        580                 585                 590

Val Ser Gly Ser Ser Val Ser Gly Leu Gly Val Ser Gly Leu Gly Val
    595                 600                 605

Ser Gly Ser Ser Val Ser Gly Leu Gly Val Ser Gly Ser Ser Val Ser
610                 615                 620

Gly Leu Gly Val Ser Gly Ser Ser Val Ser Gly Leu Gly Val Ser Gly
625                 630                 635                 640

Ser Ser Val Ser Gly Leu Gly Val Ser Gly Ser Ser Val Ser Gly Leu
            645                 650                 655

Gly Val Ser Gly Ser Ser Asp Lys Pro Asn Lys Glu Leu Leu Ser Ile
        660                 665                 670

Leu Met Glu Gly Leu Val Ala Ala Leu Glu Ala Leu Asn Ala Ala Lys
    675                 680                 685

Ile Ser Gly Phe Arg Asp Asp Tyr Tyr Val Pro Ser Asp Val Pro Val
690                 695                 700

Tyr Thr Ser Phe Leu Ser Glu Ile Leu Tyr
705                 710

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
cagaagaacc cgaaacaccg agtccagaaa c                                      31

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
gtttctggac tcggtgtttc gggttcttct g                                      31

<210> SEQ ID NO 7
<211> LENGTH: 22
<212> TYPE: DNA
<213> ORGANISM: Artificial Sequence
<220> FEATURE:
<223> OTHER INFORMATION: primer

```
<400> SEQUENCE: 7
ggtgtagttg ttggttcttc cg                                          22

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ccactaaacc ttccattaag                                             20

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
cctaacatct tccggtaatt catcg                                       25

<210> SEQ ID NO 10
<211> LENGTH: 5
<212> TYPE: PRT
<213> ORGANISM: Nephila clavipes

<400> SEQUENCE: 10

Gly Ser Ser Val Ser
 1               5

<210> SEQ ID NO 11
<211> LENGTH: 4
<212> TYPE: PRT
<213> ORGANISM: Nephila clavipes

<400> SEQUENCE: 11

Gly Leu Gly Val
 1

<210> SEQ ID NO 12
<211> LENGTH: 9
<212> TYPE: PRT
<213> ORGANISM: Nephila clavipes

<400> SEQUENCE: 12

Gly Ser Ser Val Ser Gly Leu Gly Val
 1               5

<210> SEQ ID NO 13
<211> LENGTH: 5
<212> TYPE: PRT
<213> ORGANISM: Nephila clavipes

<400> SEQUENCE: 13

Ala Gly Pro Gly Thr
 1               5
```